US008241214B2

(12) United States Patent
Kobayashi et al.

(10) Patent No.: US 8,241,214 B2
(45) Date of Patent: Aug. 14, 2012

(54) ULTRASONIC IMAGING APPARATUS AND METHOD FOR ULTRASONIC IMAGING

(75) Inventors: Yutaka Kobayashi, Tochigi-ken (JP); Takanobu Uchibori, Tochigi-ken (JP); Taketoshi Nagai, Tochigi-ken (JP); Koichi Sato, Tochigi-ken (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 703 days.

(21) Appl. No.: 11/213,875

(22) Filed: Aug. 30, 2005

(65) Prior Publication Data

US 2006/0058662 A1 Mar. 16, 2006

(30) Foreign Application Priority Data

Aug. 31, 2004 (JP) ................. 2004-252669

(51) Int. Cl.
*A61B 8/00* (2006.01)
*A61B 8/14* (2006.01)
*G06K 9/00* (2006.01)
(52) U.S. Cl. ....................... 600/437; 382/128
(58) Field of Classification Search .......... 600/437, 600/440–457; 382/100, 128, 130–134
See application file for complete search history.

(56) References Cited

U.S. PATENT DOCUMENTS

| 6,322,510 | B1 * | 11/2001 | Kataoka et al. | 600/453 |
| 6,595,921 | B1 * | 7/2003 | Urbano et al. | 600/437 |
| 2002/0035326 | A1 * | 3/2002 | Kamiyama | 600/437 |
| 2002/0123688 | A1 * | 9/2002 | Yamauchi | 600/443 |

FOREIGN PATENT DOCUMENTS

| JP | 3-90141 | 4/1991 |
| JP | 11-7428 | 1/1999 |

* cited by examiner

*Primary Examiner* — Long V. Le
*Assistant Examiner* — Lawrence Laryea
(74) *Attorney, Agent, or Firm* — Oblon, Spivak, McClelland, Maier & Neustadt, L.L.P.

(57) ABSTRACT

A ultrasonic imaging apparatus comprises an ultrasonic probe including a plurality of ultrasonic transducers which perform ultrasonic transmission and reception to an object, a transceiver unit configured to obtain an ultrasonic signal from the object by driving the plurality of ultrasonic transducers, an ultrasonic data generation unit configured to generate ultrasonic data based on the ultrasonic signal, a time information generation unit configured to generate time information related to the ultrasonic transmission or reception and a time information addition unit configured to add the time information in a part of pixel data of the ultrasonic data in order to synchronize the Image data with biomedical signal, such as ECG.

32 Claims, 14 Drawing Sheets

TIME INFORMATION STORAGE AREA

ULTRASONIC IMAGING APPARATUS AND METHOD FOR ULTRASONIC IMAGING

CROSS-REFERENCE TO RELATED APPLICATIONS

This application is based upon and claims the benefit of priority from prior Japanese Patent Application No. P2004-252669 filed on Aug. 31, 2004, the entire contents of which are incorporated herein by reference.

FIELD OF THE INVENTION

The present invention is related to an ultrasonic imaging apparatus and a method for ultrasonic imaging.

BACKGROUND

An ultrasonic imaging apparatus transmits an ultrasonic wave generated by an ultrasonic transducer in an ultrasonic probe into a patient, receives a reflective wave produced according to difference of sound impedance of a tissue of the patient with the ultrasonic transducer, and displays an image on a monitor. Since a 2-dimensional image data is easily obtained in real time by easy operation of contacting the ultrasonic probe for a body surface of the patient, this imaging method is widely used for functional diagnosis or morphological diagnosis of internal organs, such as a heart.

The ultrasonic imaging method in which living body information is obtained according to the reflective wave from the tissue or blood cell of the patient is developed by two big technical developments of an ultrasonic pulse reflective method and an ultrasonic Doppler method, and B-mode image data and Color Doppler image data which are obtained the above methods, respectively, are very important for the ultrasonic imaging.

In the ultrasonic imaging method, a method for synchronizing the above image data obtained by the transmission-and-reception wave of the ultrasonic wave to the patient with biomedical signal, such as electro cardiographic wave (ECG signal) to display the imaged data and the biomedical signal is conventionally used. Especially, it is useful that the image data and the biomedical signal are displayed simultaneously for seeing a timing of the image data in a cardiovascular diagnosis, for example.

However, it is difficult that the B mode image data or the Colored Doppler image data is displayed with the ECG signal simultaneously, since it takes longer to make the 2-dimensional image data than to make the ECG signal.

In order to solve such a problem, a method in which the image data and the ECG signal are synchronized by delaying the ECG signal is disclosed in Japanese Patent Disclosure (Kokai) No. 3-90141.

As a method for synchronizing medical information obtained from a plurality of medical apparatuses which are connected via a network, Japanese Patent Disclosure (Kokai) No. 11-7428 discloses that internal clocks, each of which is located in the each medical apparatus, are corrected according to a standard time information of a standard clock equipment connected to each apparatus via the network.

However, in the method disclosed in Japanese Patent Disclosure (Kokai) No. 3-90141, rough time for making the image data is presumed, the ECG signal is delayed for the rough time, and therefore, sufficient synchronous accuracy is not acquired. Furthermore, this method is for correcting the delay time of the image data to the ECG signal in a predetermined procedure, and it is based on the premise that the image data and the ECG signal are made and displayed in real time. In the method disclosed in Japanese Patent Disclosure (Kokai) No. 11-7428, the synchronous correction is performed to the medical information of the image data which is already made.

By the way, in a recent ultrasonic imaging apparatus, it is known that ultrasonic data which is an unit of data in each scanning direction used for generation of image data, the unit of data hereinafter called RAW data, is temporally stored in a memory in the apparatus and some days later, various signal processes are performed to the RAW data to make desired image data or analysis data. According to this method, it is possible to perform the signal processing to the RAW data anytime without the patient.

Thus, a conventional example using the RAW data is shown below. FIG. 1 is a block diagram showing a conventional ultrasonic imaging apparatus, FIG. 2 shows a composition of the RAW data stored in RAW data memory 1302, and FIG. 3 is a flow charts of operation of the ultrasonic imaging apparatus.

An ultrasonic imaging apparatus 1100 shown in FIG. 1 includes an ultrasonic probe 1201 which performs transmission-and-reception of ultrasonic wave to and from a patient, a transceiver part 1200 which performs transmission of a drive signal and reception of a reflective signal to and from the ultrasonic probe 1201, and a RAW data generation part 1250 which performs signal processing to the received signal of the transceiver part 1200 to generate RAW data, such as B-mode RAW data, I/Q signal and Color Doppler RAW data. Furthermore, the ultrasonic imaging apparatus 1100 includes a time information addition part 1301 which adds time information supplied from a time information generation part 1312 to the RAW data, and a RAW data memory part 1302 which stores the RAW data, with which the time information is added, per a scanning direction (raster).

Moreover, the ultrasonic imaging apparatus includes a biomedical signal measurement part 1311 which collects a biomedical signal, such as an ECG signal, from the patient, a time information generation part 1312 which generates time information using the biomedical signal, a biomedical signal memory part 1313 which matches and stores the biomedical signal and the time information, and an image data/analysis data generation part 1300 which reads two or more RAW data and generates the image data or the analysis data in a predetermined timing of the biomedical signal based on the time information among the RAW data stored in the RAW data memory part 1302. The ultrasonic imaging apparatus further includes a display data generation part 1305 which combines the image data or the analysis data with the biomedical signal in the predetermined timing and generates display data, a display part 1306 which displays the display data, an input part 1307 which is used for selecting an image data generation mode and for inputting various command signals, and a system control part 1308 which totally controls each above-mentioned part.

The time information addition part 1301 adds the time information (synchronized signal) which is generated based on the biomedical signal of the patient by the time information generation part 1312 to each RAW data, in the scanning direction, generated by the RAW data generation part 1250. The RAW data memory part 1302 sequentially stores the RAW data with which the time information is added.

FIG. 2 shows the composition of the RAW data stored in the RAW data memory part 1302. An vertical axis corresponds to an arrangement of the RAW data of the scanning directions θ1 to θM, and a horizontal axis corresponds to the scanning direction of the ultrasonic transmission-and-reception wave. For example, in M RAW data B-1 to B-M used for making B-mode image data of one frame, pixels a11 to a1L of RAW data B-1, each of which being 12 bits, are generated by the ultrasonic transmission-and-reception in the first scanning direction θ1. A header of the L pixels includes a time information storage area a10a in which the time information is added and a scanning information storage area a10b in which the information about the scanning directional is stored.

Similarly, headers of the RAW data B-2 to B-M in the second scanning direction θ2 to the Mth scanning direction θM include the time information storage area a20a to aM0a, the scanning information storage area a20b or aM0b, and the RAW data pixels storage area for the B mode image am1 to amL (m=2 to M).

In the RAW data memory part 1302, after scanning the RAW data B-1 to B-M in the Mth scanning direction, the RAW data B-1 to B-M for the next B-mode are stored, repeatedly.

And "1" is added to the time information storage area a30a of the RAW data (for example, RAW data B-3) obtained when an R-wave in the ECG signal of the patient is measured, and "0" is added to other time information storage areas.

The biomedical signal measurement part 1311 of FIG. 1 measures the ECG signal from the patient, and the measured biomedical signal is changed into a digital signal by an A/D converter. The time information generation part 1312 has a function for generating the time information (synchronized signal), and for example, when the biomedical signal is the ECG signal, the time information generation part 1312 detects the timing of the R-wave in the ECG signal.

The biomedical signal memory part 1313 matches and stores the biomedical signal supplied from the biomedical signal measurement part 1311 and the time information which the time information generation part 1312 generates based on the biomedical signal.

The image data/analysis data generation part 1300 reads out one or more RAW data in a predetermined timing among the RAW data stored in the RAW data memory part 1302, performs data processing to the read out RAW data, and executes a scan conversion to make the image data.

This image data/analysis data generation part 1300 includes a RAW data processing part 1303 and an image data generation part 1304. The RAW data processing part 1303 reads out the RAW data in the predetermined timing based on the time information added to the RAW data, and performs data processing, such as image processing or analyzing of the RAW data for the B-mode image or the Color Doppler image and spectrum analyzing of the I/Q signal. The image data generation part 1304 performs the scan conversion of the B-mode RAW data or the Color Doppler RAW data which are read out by the RAW data processing part 1303 to make the image data.

The display data generation part 1305 includes an operation circuit and a memory circuit, and the operation circuit reads the biomedical signal in the same timing as the image data supplied from the image data generation part 1304 of the image data/analysis data generation part 1300 or the analysis data supplied from the RAW data processing part 1303. Subsequently, the display data generation part 1305 generates the display data by combining the image data or the analysis data supplied from the image data/analysis data generation part 1300 with the biomedical signal, and temporally stores the display data in the memory circuit.

The display part 1306 includes a conversion circuit and a monitor. In the conversion circuit, D/A conversion and television format conversion execute to the display data generated in the display data generation part 1305, and the converted data is displayed on the monitor, such as CRT or Liquid Crystal Display.

The input part 1307 includes an input device, such as a keyboard, a trackball and a mouse, and a display panel on a navigational panel. An input of patient information or various command signals, selection of image data generation mode, etc. are performed using the input device and the display panel.

Moreover, the system control part 1308 includes a CPU and a memory circuit, and various kinds of inputted information and selection information, etc. which are supplied from the input part 1307 are stored in the memory circuit. The CPU controls each part of a whole apparatus, such as the transceiver part 1200, the RAW data generation part 1250, the time information addition part 1301, the image data/analysis data generation part 1300, the display data generation part 1305, and the display part 1306.

Next, an basic operation of the ultrasonic imaging apparatus 100 and a flow of a synchronous display of the image data and biomedical signal which are obtained by the ultrasonic imaging apparatus 1100 are explained in FIG. 1 through FIG. 3. It is explained below in FIG. 3 that B-mode image data generated from the B-mode RAW data obtained by the ultrasonic transmission-reception to and from the patient and the ECG signal obtained in parallel to the ultrasonic transmission-reception are displayed synchronously.

Before the ultrasonic wave is transmitted and received to and from the patient, a doctor or a sonography technologist (hereafter called an operator) sets electrodes of the biomedical signal measurement part (electrocardiograph) 1311 at a predetermined position of the patient. Next, the operator inputs the patient information or selects the image data generation mode, such as B-mode image data with the input device of the input part 1307, and sets a tip part of the ultrasonic probe 1201 at a predetermined position of the patient (Step S1 of FIG. 3). At this time, the inputted or selected information is stored in the memory circuit of the system control part 1308.

After the initial setting is completed, the transmission and reception of the ultrasonic pulse are performed to and from the patient, based on control of the system control part 1308. The received ultrasonic signal is sent to the B-mode signal generation part of the RAW data generation part 1250.

The B-mode signal generation part executes an envelope detection, logarithm conversion and A/D conversion to the inputted data to generate B-mode RAW data to be supplied to the time information addition part 1301. The B-mode RAW data, as shown in FIG. 2, includes pixels a11 to a1L and a header, amplitude of the A/D converted signal is stored in the pixels a11 to a1L as 12 bits data, and information about the first scanning direction (θ1) is stored in the scanning information storage area a 10b of the header (Step S2 of FIG. 3).

On the other hand, in parallel to the ultrasonic transmission-and-reception in the first scanning direction (θ1), the biomedical signal measurement part 1311 measures the ECG signal of the patient (Step S3 of FIG. 3), and the acquired ECG signal is supplied to the time information generation part 1312. The time information generation part 1312 which receives the ECG signal determines whether the timing of the ultrasonic transmission-and-reception corresponds to the R-wave of the ECG signal, generates the time information based on the determination, and sends the time information to the time information addition part 1301 and the biomedical signal memory part 1313. (Step S4 of FIG. 3).

Subsequently, the time information addition part 1301 adds the time information supplied from the time information generation part 1312 to the time information storage area a10a of the B-mode RAW data (B-mode RAW data B-1 in FIG. 2) in the first scanning direction supplied from the B-mode data generation part 1204 of the RAW data generation part 1250 (Step S5 of FIG. 3). In this case, when the timing of the ultrasonic transmission-and-reception does not corresponds to the R-wave of the ECG signal, as shown in FIG. 2, the time information "0" is added to the time information storage area a10a of the RAW data B-1. Otherwise, the time information "1" is added. The B-mode RAW data with which the time information is added is stored in the RAW data memory part 1302 (Step S6 of FIG. 3).

The time information is added to the ECG signal data supplied to the biomedical signal memory part 1313, and the ECG signal data is stored. (Steps S7 and S8 of FIG. 3).

Similarly, the system control part 1308 performs the ultrasonic transmission-and-reception also in the second scanning direction through the Mth scanning direction, and after the Mth scanning direction, the ultrasonic transmission-and-reception is performed in the first scanning direction through Mth scanning direction repeatedly. Each B-mode RAW data, obtained at this time, with which the time information is added in the time information addition part 1301 is stored in the RAW data memory part 1302, and the ECG signal obtained in parallel to the generating or the storing of the B-mode RAW data with which the time information is added is stored in the biomedical signal memory part 1313.

The RAW data processing part 1303 of the image data/analysis data generation part 1300 confirms the time information of the RAW data B-1, B-2, etc. which are stored in the RAW data memory part 1302 in FIG. 2. When the time information "1" indicating the R wave of the ECG signal is confirmed in the RAW data B-3, for example, RAW data is read out one by one on the basis of the RAW data B-3. Subsequently, the RAW data processing part 1303 performs image processing to the read out RAW data, and supplies the RAW data to the image data generation part 1304.

The image data generation part 1304 performs the scanning conversion to one frame of the B-mode RAW data, in a predetermined timing, which is read out by the RAW data processing part 1303, and generates one frame of the B-mode image data (Step S9 of FIG. 3).

The display data generation part 1305 reads out a series of the ECG signal one by one on the basis of the ECG signal (R-wave) with which the time information "1" is added among the ECG signal stored in the biomedical signal memory part 1313 where the time information is added (Step S10 of FIG. 3). And the display data generation part 1305 combines the B-mode image data supplied from the image data generation part 1304 of the image data/analysis data generation part 1300 with the R-wave of the ECG signal such that the timing of display of the B-mode image data in the third direction θ3 is synchronized with the timing of display of the R-wave of the ECG signal and generates display data.

The display part 1306 executes the D/A conversion, the television format conversion to the display data generated in the display data generation part 1305, generates a display signal and displays the display signal on the monitor (Step S11 of FIG. 3).

According to the above mentioned conventional example, the accuracy may be low since the time information is obtained from the ECG signal, or a large memory space in the header may be required, since the time information is added to the header of the RAW data.

SUMMARY

An object of the present invention is to ameliorate at least one of the above-mentioned problems, such as improvement of synchronization of image data or analysis data and an ECG signal or reduction of memory space in a header.

According to one aspect of the present invention, there is provided an ultrasonic imaging apparatus comprises an ultrasonic probe including a plurality of ultrasonic transducers which perform ultrasonic transmission and reception to an object, a transceiver unit configured to obtain an ultrasonic signal from the object by driving the plurality of ultrasonic transducers, an ultrasonic data generation unit configured to generate ultrasonic data based on the ultrasonic signal, a time information generation unit configured to generate time information related to the ultrasonic transmission or reception and a time information addition unit configured to add the time information in a part of pixel data of the ultrasonic data.

According to another aspect of the present invention, there is provided an ultrasonic imaging apparatus comprises an ultrasonic probe including a plurality of ultrasonic transducers which perform ultrasonic transmission and reception to an object, a transceiver unit configured to obtain an ultrasonic signal from the object by driving the plurality of ultrasonic transducers, an ultrasonic data generation unit configured to generate ultrasonic data based on the ultrasonic signal, a standard time information generation unit configured to generate standard time information, a biomedical signal measurement configured to measure a biomedical signal of the object, a first time information addition unit configured to add the standard time information to the ultrasonic data and a second time information addition unit configured to add the standard time information to biomedical data corresponding to the biomedical signal.

According to another aspect of the present invention, there is provided an ultrasonic imaging apparatus comprises an ultrasonic probe including a plurality of ultrasonic transducers which perform ultrasonic transmission and reception to an object, a transceiver unit configured to obtain an ultrasonic signal from the object by driving the plurality of ultrasonic transducers, an ultrasonic data generation unit configured to generate ultrasonic data based on the ultrasonic signal, a biomedical signal measurement configured to measure a biomedical signal of the object and a biomedical data addition unit configured to add biomedical data corresponding to the biomedical signal to the ultrasonic data.

According to another aspect of the present invention, there is provided a method for ultrasonic imaging comprises performing ultrasonic transmission and reception to an object by an ultrasonic probe including a plurality of ultrasonic transducers, obtaining an ultrasonic signal from the object by driving the plurality of ultrasonic transducers, generating ultrasonic data based on the ultrasonic signal, generating time information related to the ultrasonic transmission or reception and adding the time information in a part of pixel data of the ultrasonic data.

According to another aspect of the present invention, there is provided a method for ultrasonic imaging comprises performing ultrasonic transmission and reception to an object by an ultrasonic probe including a plurality of ultrasonic transducers, obtaining an ultrasonic signal from the object by driving the plurality of ultrasonic transducers, generating ultrasonic data based on the ultrasonic signal, generating standard time information, measuring a biomedical signal of the object, adding the standard time information to the ultrasonic data and adding the standard time information to biomedical data corresponding to the biomedical signal.

According to another aspect of the present invention, there is provided a method for ultrasonic imaging comprises performing ultrasonic transmission and reception to an object by an ultrasonic probe including a plurality of ultrasonic transducers, obtaining an ultrasonic signal from the object by driving the plurality of ultrasonic transducers, generating ultrasonic data based on the ultrasonic signal, measuring a biomedical signal of the object and adding biomedical data corresponding to the biomedical signal to the ultrasonic data.

According to another aspect of the present invention, there is provided an ultrasonic imaging apparatus comprises an ultrasonic probe including a plurality of ultrasonic transducers which perform ultrasonic transmission and reception to an object, a transceiver unit configured to obtain an ultrasonic signal from the object by driving the plurality of ultrasonic transducers, an ultrasonic data generation unit configured to generate ultrasonic data based on the ultrasonic signal, a biomedical signal measurement configured to measure a biomedical signal of the object and a biomedical data addition unit configured to add biomedical data corresponding to the biomedical signal to the ultrasonic data under a condition where an addition timing of the biomedical signal to the ultrasonic data is adjusted based on a condition of the ultrasonic transmission and reception.

According to another aspect of the present invention, there is provided a method for ultrasonic imaging comprises performing ultrasonic transmission and reception to an object by an ultrasonic probe including a plurality of ultrasonic transducers, obtaining an ultrasonic signal from the object by driving the plurality of ultrasonic transducers, generating ultrasonic data based on the ultrasonic signal, measuring a biomedical signal of the object and adding biomedical data corresponding to the biomedical signal to the ultrasonic data under a condition where an addition timing of the biomedical signal to the ultrasonic data is adjusted based on a condition of the ultrasonic transmission and reception.

DETAILED DESCRIPTION OF EXEMPLARY EMBODIMENTS

Figure 1:
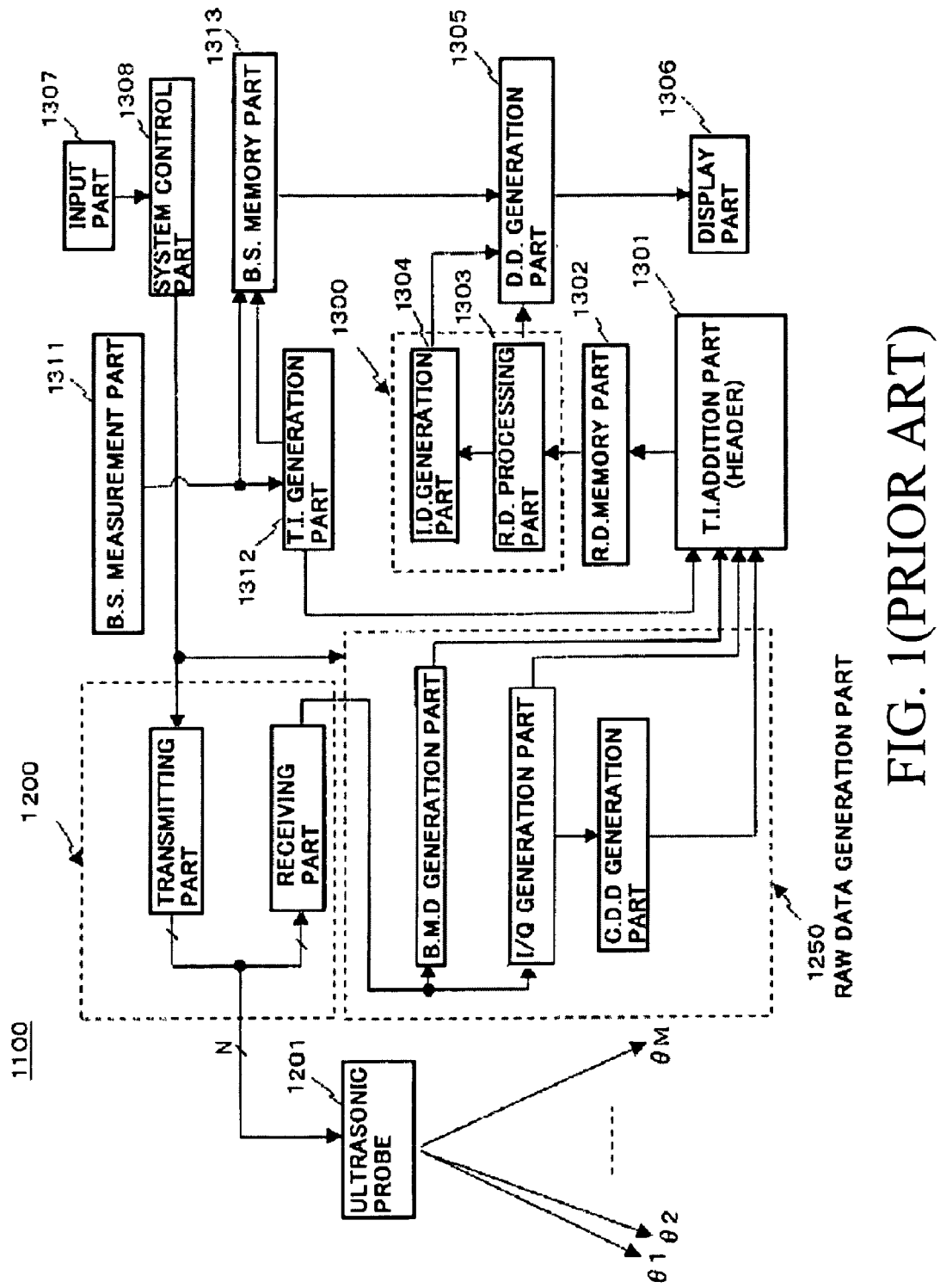
FIG. 1 is a block diagram showing a whole conventional ultrasonic imaging apparatus.
Figure 2:
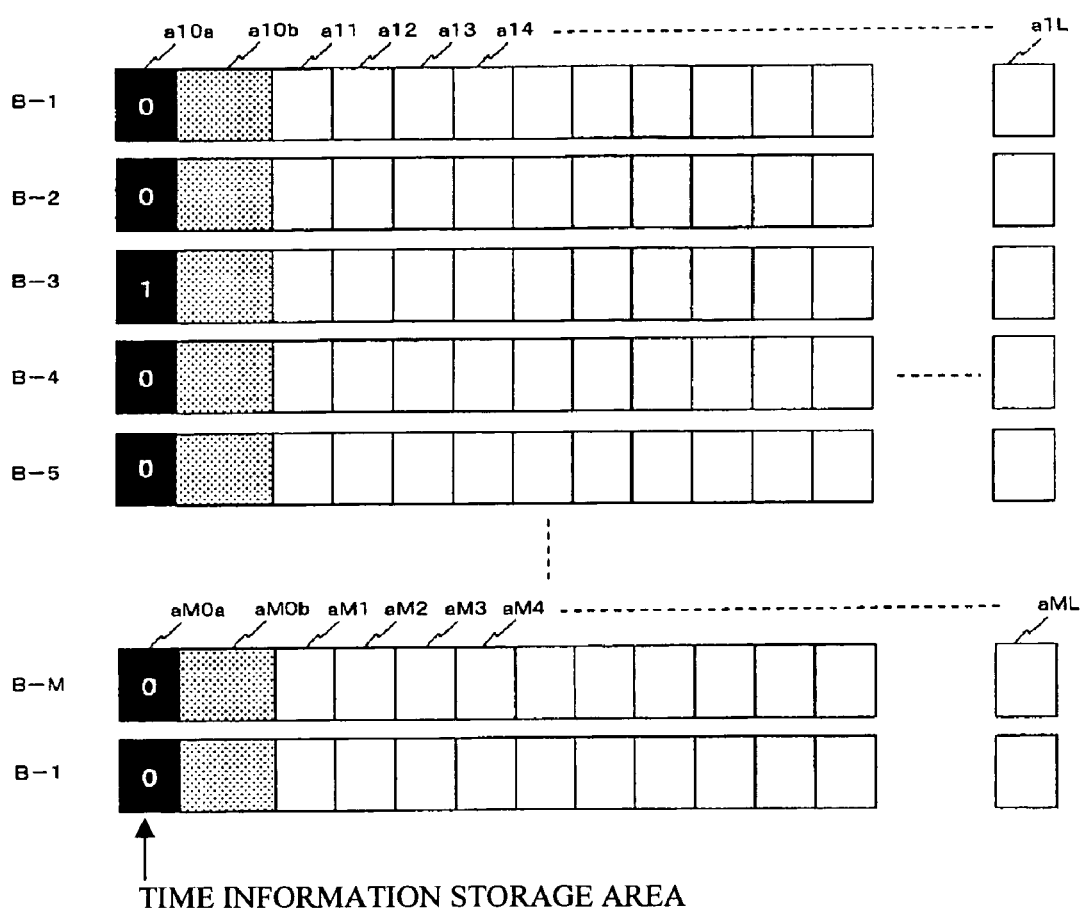
FIG. 2 is an illustration showing a composition of RAW data with time information is added in the conventional ultrasonic imaging apparatus.
Figure 3:
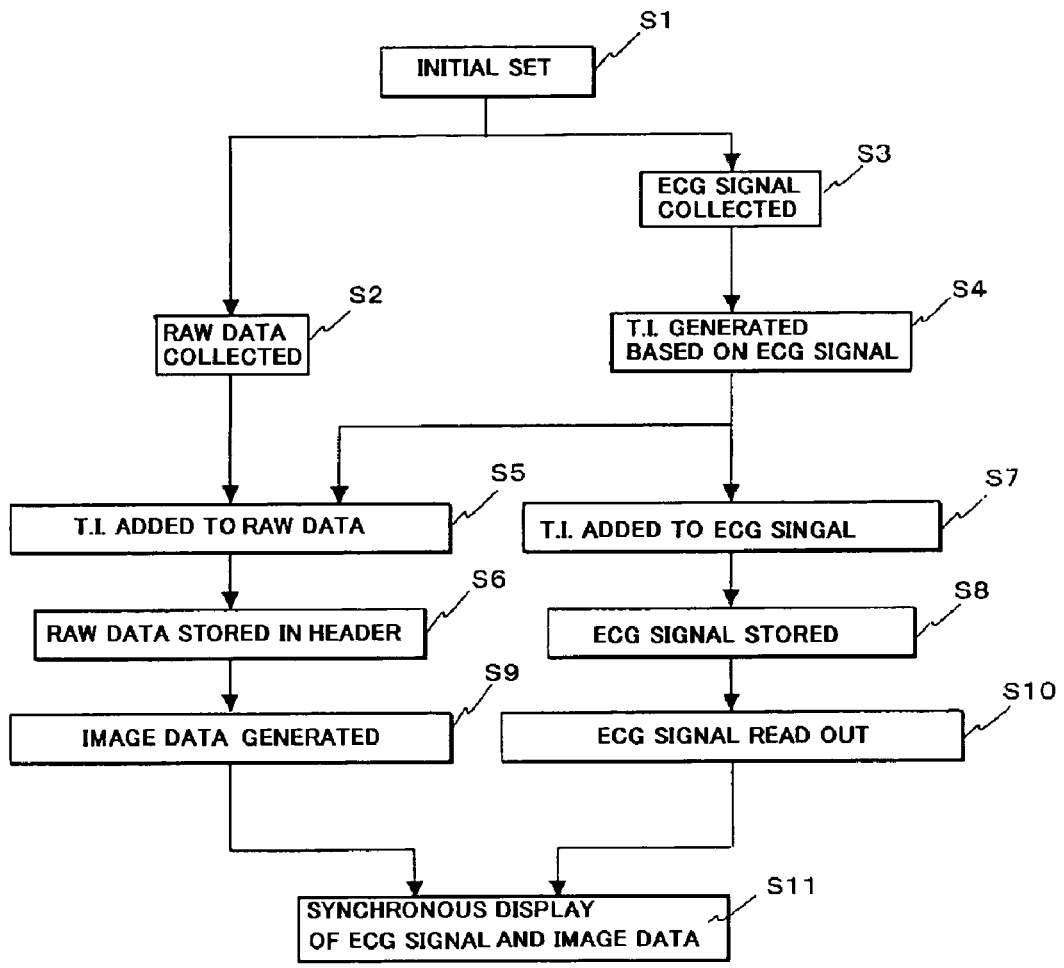
FIG. 3 is a flow chart showing a procedure of synchronized display of image data and a biomedical signal in the conventional ultrasonic imaging apparatus.

Hereafter, with reference to drawings, embodiments and modifications are explained. In the above-mentioned conventional example, the time information of the ECG signal supplied from the time information generation part 1312 is stored in the time information storage in the header of the B-mode RAW data, as shown in FIG. 2. On the other hand, in the first embodiment, the time information is added and stored at a part of pixel of the B-mode RAW data.

With reference to FIG. 4 through FIG. 8, an ultrasonic imaging apparatus in the first embodiment is explained below.

Figure 4:
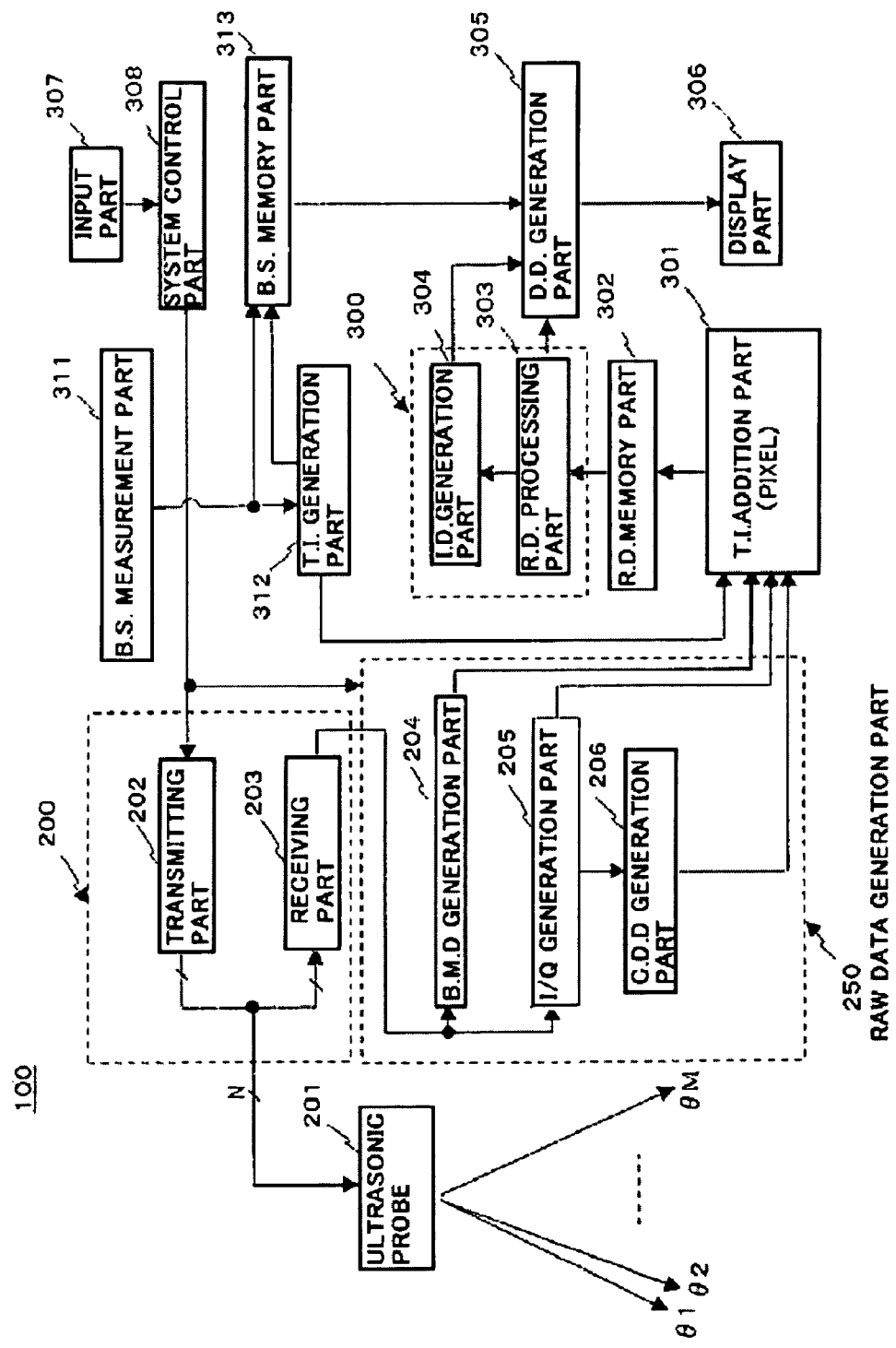
FIG. 4 is a block diagram showing a whole ultrasonic imaging apparatus in a first embodiment.

An ultrasonic imaging apparatus 100 shown in FIG. 4 includes an ultrasonic probe 201 which performs transmission-and-reception of ultrasonic wave to and from a patient, a transceiver part 200 which performs transmission of a drive signal and reception of a reflective signal to and from the ultrasonic probe 201, and a RAW data generation part 250 which performs signal processing to the received signal of the transceiver part 200 to generate RAW data, such as B-mode RAW data, I/Q signal and Color Doppler RAW data.

Furthermore, the ultrasonic imaging apparatus 100 includes a time information addition part 301 which adds time information supplied from a time information generation part 312 to the RAW data, and a RAW data memory part 302 which stores the RAW data, with which the time information is added, per a scanning direction (raster).

Moreover, the ultrasonic imaging apparatus 100 includes a biomedical signal measurement part 311 which collects a biomedical signal, such as an ECG signal, from the patient, a time information generation part 312 which generates time information using the biomedical signal, a biomedical signal memory part 313 which matches and stores the biomedical signal and the time information, and an image data/analysis data generation part 300 which reads two or more RAW data and generates the image data or the analysis data in a predetermined timing of the biomedical signal based on the time information among the RAW data stored in the RAW data memory part 302. The ultrasonic imaging apparatus further includes a display data generation part 305 which combines the image data or the analysis data with the biomedical signal in the predetermined timing and generates display data, a display part 306 which displays the display data, an input part 307 which is used for selecting an image data generation mode and for inputting various command signals, and a system control part 308 which totally controls each above-mentioned part.

The ultrasonic probe 201 which contacts a front of a surface of the patient, transmits and receives the ultrasonic wave includes a plurality of ultrasonic transducers (N pieces) which are located on a tip of the ultrasonic probe 201 and are arranged in one (or two) direction(s). The ultrasonic transducer which is an electro acoustic transducer, for example, changes an electric pulse (drive signal) into an ultrasonic pulse (transmitted ultrasonic wave) at a time of transmission, and changes an ultrasonic reflective wave (received ultrasonic wave) into an electric signal (received signal) at a time of reception. This ultrasonic probe 201 is small and lightweight, and is connected to the transceiver part 200 through cables of N channels. The ultrasonic probe 201 includes a sector scanning probe, a linear scanning probe, a convex scanning probe, etc. and one probe is arbitrarily selected from these ultrasonic probes according to a diagnostic part, for example. It is explained below that the ultrasonic probe 201 is a sector scanning probe as an example.

Figure 5:
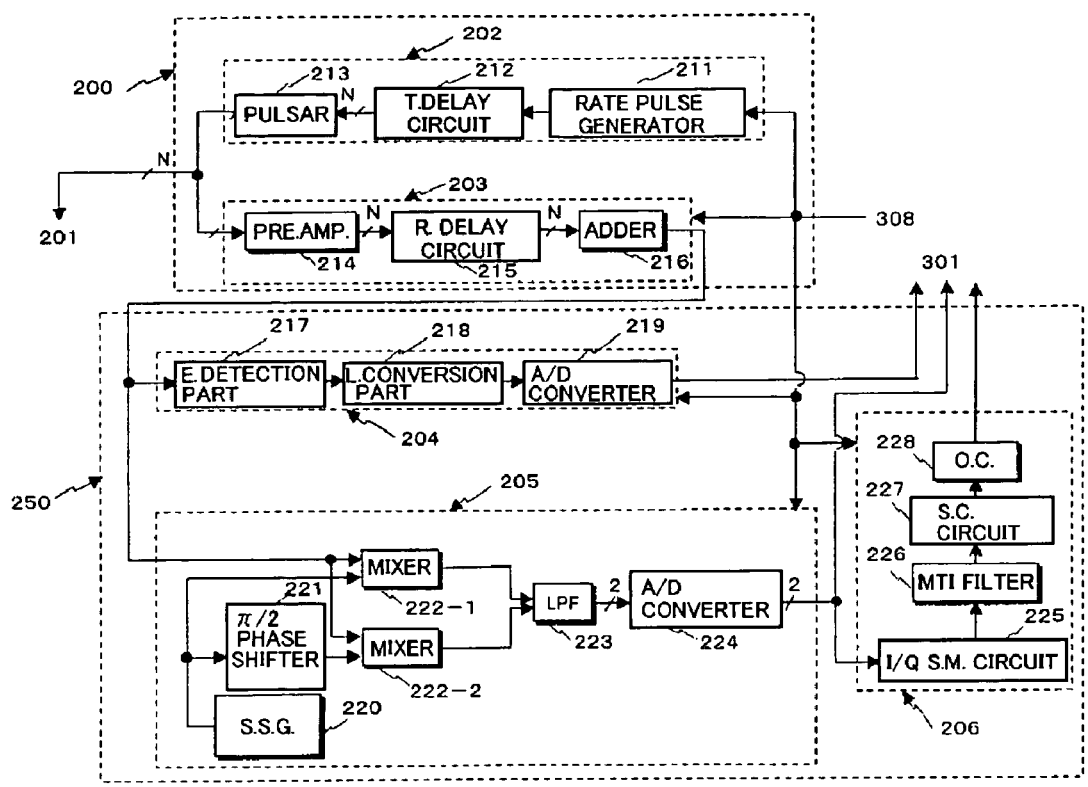
FIG. 5 is a block diagram showing a transceiver part and a RAW data generation part in the first embodiment.

The transceiver part 200 includes an ultrasonic transmitting part 202 which generates the drive signal for generating the transmitted ultrasonic wave, and an ultrasonic receiving part 203 which performs a phase adjusted addition of the received signals of two or more channels obtained from the ultrasonic transducers of the ultrasonic probe 201, as shown in FIG. 5. The ultrasonic transmitting part 202 includes a rate pulse generator 211, a transmitting delay circuit 212, and a pulsar 213. The rate pulse generator 211 supplies a rate pulse which determines a repetition cycle (Tr) of the ultrasonic pulse transmitted to the patient to the transmitting delay circuit 212. The transmitting delay circuit 212 includes the same number (N channels) of independent delay circuits as the number of the ultrasonic transducers used for transmission in the ultrasonic probe 201, and gives delay time for focusing the ultrasonic wave to a desired depth in order to obtain a thin beam width in transmission and delay time for deflecting the ultrasonic wave in a desired direction to the rate pulse to be supplied to the pulsar 213.

The pulsar 213 includes the same number of independent drive circuits (N channels) as the number of the ultrasonic transducers used for transmission and generates drive pulses for driving N number of the ultrasonic transducers, and the ultrasonic wave is transmitted to the patient.

The ultrasonic receiving part 203 includes a preamplifier 214 of N channels, a reception delay circuit 215, and an adder 216. The preamplifier 214 amplifies the minute received signal changed into the electric signal by the ultrasonic transducer, and sufficient S/N is obtained. The reception delay circuit 215 gives delay time for focusing the received ultrasonic wave from a desired depth in order to obtain a thin beam width in reception and delay time for deflecting the received ultrasonic wave in a desired direction to output of the preamplifier 214. Thereafter, the output is supplied to the adder 216, and in the adder 216, the received signals of N channels from the ultrasonic transducers are added into one group of signals.

The RAW data generation part 250 includes a B-mode data generation part 204 which performs signal processing for generating RAW data of B-mode image according to the received signal of the ultrasonic receiving part 203, an I/Q signal generation part 205 which generates an I/Q signal to the above-mentioned received signal, and an Color Doppler data generation part 206 which performs signal processing for generating RAW data of Color Doppler image according to the I/Q signal.

The B-mode signal generation part 204 includes an envelope detection part 217, a logarithm conversion part 218 and an A/D converter 219. Inputted signal into the B-mode data generation part 204 is processed by the envelope detection part 217 and subsequently by the logarithm conversion part 218 and a minute signal is emphasized, relatively. An output of the logarithm conversion part 218 is processed by the A/D converter 219 to generate B-mode image data.

The I/Q signal generation part 205 includes a standard signal generator 220, a π/2 phase shifter 221, mixers 222-1 through 222-2, two channel low pass filter (LPF) 223 and an A/D converter 224. And rectangular phase detection is performed to the received signal of the ultrasonic wave, and IQ component of the received signal is detected.

That is, the output signal of the ultrasonic receiving part 203 is inputted into first terminals of mixers 222-1 and 222-2. An continuous wave output of the standard signal generator 220 has frequency almost equal to a center frequency of the inputted signal, and is synchronized with the rate pulse of the rate pulse generator 211. The continuous wave is supplied to a second terminal of the mixer 222-1 and the π/2 phase shifter 221. In the π/2 phase shifter 221, a phase of the signal is shifted 90 degrees and is supplied to a second terminal of the mixer 222-2. The outputs of the mixers 222-1 and 222-2 are supplied to the low pass filter 223. An additional component of the inputted signal frequency component of the I/Q signal generation part 205 and the output signal frequency component of the standard signal generator is removed, and subtraction component is detected.

Subsequently, the A/D converter 224 samples the output signal of the LPF 223, namely the analog signal to which the rectangular phase detection is performed, at a predetermined sampling time, and the analog signal is converted into a digital signal.

The Color Doppler data generation part 206 includes an I/Q signal memory circuit 225, an MTI filter 226, a self-correlation circuit 227, and an operation circuit 228. I component (real number component of the received signal) and Q component (imaginary number component of the received signal) which is obtained in rectangular phase detection to the received signal obtained in two or more times of the continuous ultrasonic transmission-and-reception in the predetermined scanning direction by the I/Q signal generation part 205, are stored one by one in the I/Q signal memory circuit 225.

The MTI filter 226 of the Color Doppler data generation part 206 is a digital filter for passing high frequency. The MTI filter 226 removes a reflective component from a fixed reflector, such as an organ, and a Doppler signal component (Tissue Doppler component) which is caused by breath movement or systaltic movement, etc.

The self-correlation circuit 227 performs self-correlation processing to the Doppler signal in which a blood flow information is mainly extracted by the MTI filter 226. The operation circuit 228 calculates an average of velocity value, a distributed value, a power value, etc. of the blood flow in two dimensions based on the self-correlation processing result, and generates Color Doppler data.

In FIG. 4, the time information addition part 301 adds the time information (synchronized signal) which is generated by the time information generation part 312 based on the biomedical signal of the patient to a part of pixel of each RAW data which is generated in each scanning direction by the RAW data generation part 250. The RAW data memory part 302 stores the RAW data with which the time information is added.

Figure 8:
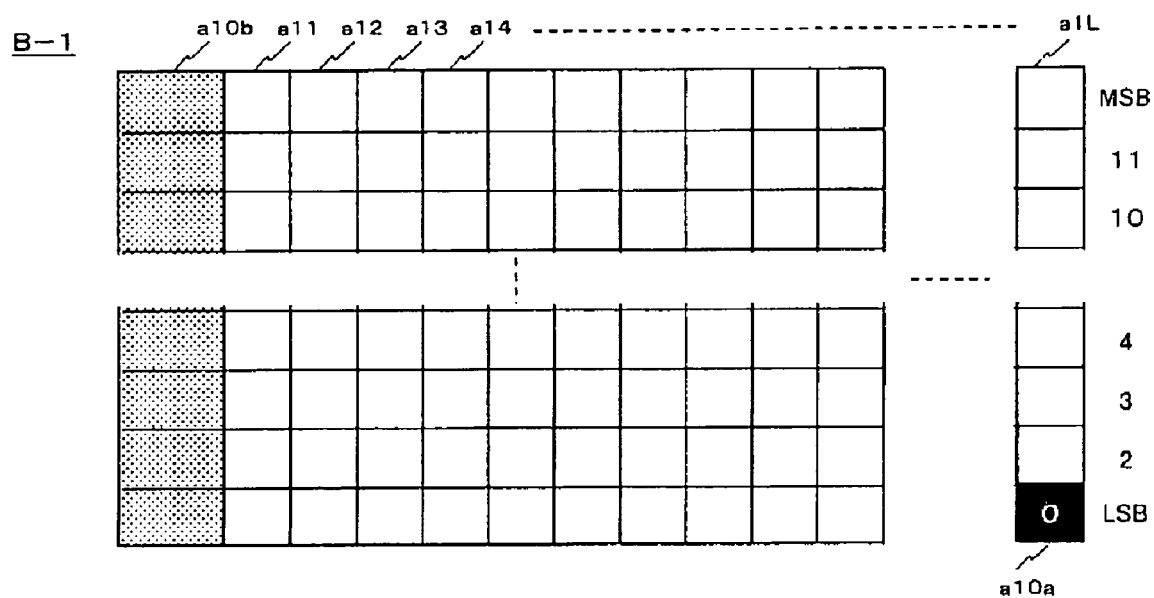
FIG. 8 is an illustration showing a composition of RAW data with time information is added in a modification of the first embodiment.

FIG. 8 is an illustration showing a composition of B-mode RAW data in the first embodiment. For example, each pixel of a11 to a1L of B-mode RAW data B-1 which is obtained in a first direction θ1 is 12 bits, and Least Significant Bit (LSB) of pixel a1L in the B-mode RAW data B-1 is set as the time information storage area a10a. That is, the time information "1" or "0" supplied from the time information generation part 312 of FIG. 4 is stored at the time information storage area a10a in the pixel a1L.

When the time information is added and stored in a part of pixel as mentioned above, the time information could influence quality of B-mode image data, for example. However, since the time information storage area a10a is only LSB, the influence is very small. Furthermore, since the pixel a1L is a pixel in which the received signal obtained the deepest portion in the patient is stored, it is unlikely that the pixel stores very important information clinically.

Similarly, the time information is added in the storage areas a20a through aM0a as parts of pixels of RAW data B-2 through B-M in a second direction θ2 through an Mth in a direction θM.

In the RAW data memory part 302, followed by the RAW data B-M in the Mth direction θM, the next B-mode RAW data B-1 or B-M is repeatedly stored.

In the time information storage area a10a of the RAW data, such as RAW data B-3, when the R-wave of the ECG signal of the patient is detected, "0" is added.

Next, the biomedical signal measurement part 311 of FIG. 4 measures the biomedical signal, such as the ECG signal, a brain wave, a heartbeat, a blood-pressure waveform, a respiratory waveform, and an impedance waveform, of the patient, and the measured biomedical signal is changed into a digital signal by the A/D converter. On the other hand, the time information generation part 312 has a function for generating time information (synchronized signal) based on the biomedical signal. The time information generation part 312 detects the timing of R-wave in the ECG signal when the biomedical signal is the ECG signal, for example.

Moreover, the biomedical signal memory part 313 matches and stores the biomedical signal supplied from the biomedical signal measurement part 311 and the time information which the time information generation part 312 generates based on the biomedical signal.

On the other hand, the image data/analysis data generation part 300 reads out one or more RAW data in a predetermined timing among RAW data stored in the RAW data memory part 302, performs data processing to the read out RAW data, and further, performs scanning conversion to generate image data.

The image data/analysis data generation part 300 includes a RAW data-processing part 303 and an image data generation part 304. The RAW data-processing part 303 reads out the RAW data in a predetermined timing based on the time information added to the RAW data, performs image processing and image analyzing to the B-mode RAW data and the Color Doppler RAW data, and performs data processing, such as spectrum analyzing to the I/Q signal. The image data generation part 304 performs scan conversion to the B-mode RAW data or the Colored Doppler RAW data, in the predetermined timing, which are read out from the RAW data-processing part 303 to generate image data.

On the other hand, the display data generation part 305 includes an operation circuit and a memory circuit, and the operation circuit reads the biomedical signal based on the time information in the same timing as the image data supplied from the image data generation part 304 of the image data/analysis data generation part 300 and the various analysis data supplied from the RAW data-processing part 303. Subsequently, the display data generation part 305 combines the image data or the analysis data supplied from the image data/analysis data generation part 300 with the biomedical signal to generate display data, and the combined data is stored in the memory circuit.

The display part 306 includes a conversion circuit and a monitor, and the display data generated in the display data generation part 305 is changed into a display signal by the D/A conversion and the television format conversion, and is displayed on the monitor, such as a CRT or a Liquid Crystal Display.

The input part 307 includes an input device, such as a keyboard, a trackball, and a mouse, etc, and a display panel, on a navigation panel, and patient information and various command signals are inputted or image data generation mode is selected with the input device and the display panel.

Moreover, the system control part 308 includes a CPU and a memory circuit, and various kinds of inputted or selected information, etc. which are supplied from the input part 307 are stored in the memory circuit. The CPU controls each part of a whole apparatus, such as the transceiver part 200, the RAW data generation part 250, the time information addition part 301, the image data/analysis data generation part 300, the display data generation part 305, and the display part 306.

Next, a basic operation of the ultrasonic imaging apparatus 100 in the first embodiment and synchronous display of the image data and biomedical signal which are obtained by the ultrasonic imaging apparatus 100 are explained with FIG. 4 through FIG. 8. Although it is explained below that the B-mode image data generated based on the B-mode RAW data in the ultrasonic transmission-and-reception is synchronously displayed with the ECG signal collected in parallel to the ultrasonic transmission-and-reception in FIG. 6 which is a flow chart, the displayed data may not be limited to the B-mode image data but the Color Doppler image data, Doppler Spectrum data or various analysis data may be used instead of or in addition to the B-mode image data. Instead of the ECG signal, other biomedical signal, such as a blood-pressure waveform may be used.

Before the ultrasonic wave is transmitted and received to and from the patient, a doctor or a sonography technologist (hereafter called an operator) sets electrodes of the biomedical signal measurement part (electrocardiograph) 311 at a predetermined position of the patient. Next, the operator inputs the patient information or selects the image data generation mode, such as B-mode image data with the input device of the input part 307, and sets a tip part of the ultrasonic probe 201 at a predetermined position of the patient (Step S1 of FIG. 6). At this time, the inputted or selected information is stored in the memory circuit of the system control part 308.

After the initial setting is completed, the system control part 308 supplies transmission and reception control signal to the rate pulse generator 211 of the ultrasonic transmitting part 202. The rate pulse generator 211 supplies a rate pulse which determines a repetition cycle (Tr) of the ultrasonic pulse transmitted to the patient to the transmitting delay circuit 212.

The transmitting delay circuit 212 gives delay time for focusing the ultrasonic wave to a desired depth and delay time for deflecting the ultrasonic wave in a desired direction to the rate pulse to be supplied to the pulsar 213. The pulsar 213 supplies a drive signal generated by drive of the rate pulse to N ultrasonic transducers in the ultrasonic probe 201 through a cable, and an ultrasonic pulse is transmitted in the θ1 direction of the patient.

A part of ultrasonic pulse transmitted to the patient is reflected in a border plane of organs or a tissue which have different sound impedance. The ultrasonic reflected wave (received ultrasonic wave) is received by the ultrasonic transducer of the ultrasonic probe 201, and is changed into an electric signal (received signal). The electric signal is amplified by the independent preamplifier 214 of N channels in the ultrasonic receiving part 203, and is sent to the reception delay circuit 215 of N channels.

The reception delay circuit 215 gives delay time for focusing the ultrasonic wave from a predetermined depth and delay time for deflecting the received ultrasonic wave in a first direction to the received signal to be send to the adder 216. In the adder 216, the received signals of N channels from the reception delay circuit 215 are added into one group of signals to be sent to the B-mode data generation part 204.

Figure 6:
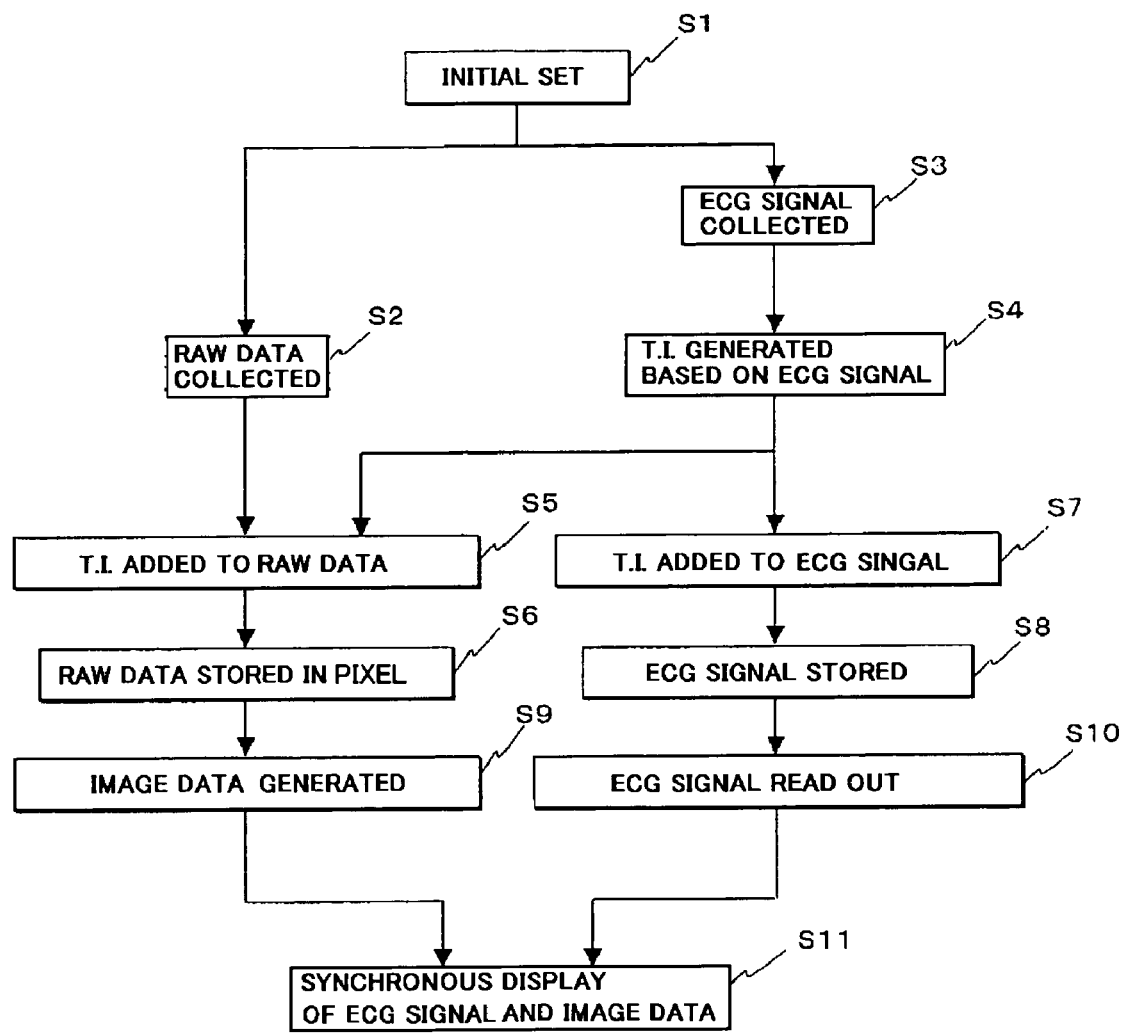
FIG. 6 is a flow chart showing a procedure of synchronized display of image data and a biomedical signal in the first embodiment.

The B-mode data generation part 204 performs an envelope detection a logarithm conversion an A/D conversion to the output signal from the adder 216, and B-mode RAW data is generated to be supplied to the time information addition part 301 (Step S2 of FIG. 6).

In parallel to the ultrasonic transmission-and-reception in the first scanning direction θ1, the biomedical signal measurement part 311 measures the ECG signal of the patient (Step S3 of FIG. 6), and the obtained ECG signal is supplied to the time information generation part 312. The time information generation part 312 which receives the ECG signal determines whether the timing of the ultrasonic transmission-and-reception corresponds to the R-wave of the ECG signal, generates the time information based on the determination, and sends the time information to the time information addition part 1301 and the biomedical signal memory part 1313. (Step S4 of FIG. 6).

Subsequently, the time information addition part 301 adds the time information supplied from the time information generation part 312 to the time information storage area a10a of the B-mode RAW data (B-mode RAW data B-1 in FIG. 8) in the first scanning direction supplied from the B-mode data generation part 204 of the RAW data generation part 250 (Step S5 of FIG. 6). In this case, when the timing of the ultrasonic transmission-and-reception does not corresponds to the R-wave of the ECG signal, as shown in FIG. 8, the time information "0" is added to the time information storage area a10a of the RAW data B-1. Otherwise, the time information "1" is added. The B-mode RAW data with which the time information is added is stored in the RAW data memory part 302 (Step S6 of FIG. 6).

The time information is added to the ECG signal data supplied to the biomedical signal memory part 1313, and the ECG signal data is stored. (Steps S7 and S8 of FIG. 6).

Similarly, the system control part 308 performs the ultrasonic transmission-and-reception also in the second scanning direction through the Mth scanning direction, and after the Mth scanning direction, the ultrasonic transmission-and-reception is performed in the first scanning direction through Mth scanning direction repeatedly. Each B-mode RAW data, obtained at this time, with which the time information is added in the time information addition part 301, is stored in the RAW data memory part 302, and the ECG signal obtained in parallel to the generating or the storing of the B-mode RAW data with which the time information is added is stored in the biomedical signal memory part 313.

The RAW data processing part 303 of the image data/analysis data generation part 300 confirms the time information of the RAW data B-1, B-2, etc. which are stored in the RAW data memory part 302. When the time information "1" indicating the R wave of the ECG signal is confirmed in the RAW data B-3, for example, RAW data is read out one by one on the basis of the RAW data B-3. Subsequently, the RAW data processing part 303 performs image processing to the read out RAW data, and supplies the RAW data to the image data generation part 304.

The image data generation part 304 performs the scanning conversion to one frame of the B-mode RAW data, in a predetermined timing, which is read out by the RAW data processing part 303, and generates one frame of the B-mode image data (Step S9 of FIG. 6).

The display data generation part 305 reads out a series of the ECG signal one by one on the basis of the ECG signal (R-wave) with which the time information "1" is added among the ECG signal stored in the biomedical signal memory part 313 where the time information is added (Step S10 of FIG. 6) And the display data generation part 305 combines the B-mode image data supplied from the image data generation part 304 of the image data/analysis data generation part 300 with the R-wave of the ECG signal such that the timing of display of the B-mode image data in the third direction θ3 is synchronized with the timing of display of the R-wave of the ECG signal and generates display data.

The display part 306 executes the D/A conversion, the television format conversion to the display data generated in the display data generation part 305, generates a display signal and displays the display signal on the monitor (Step S11 of FIG. 6).

Figure 7:
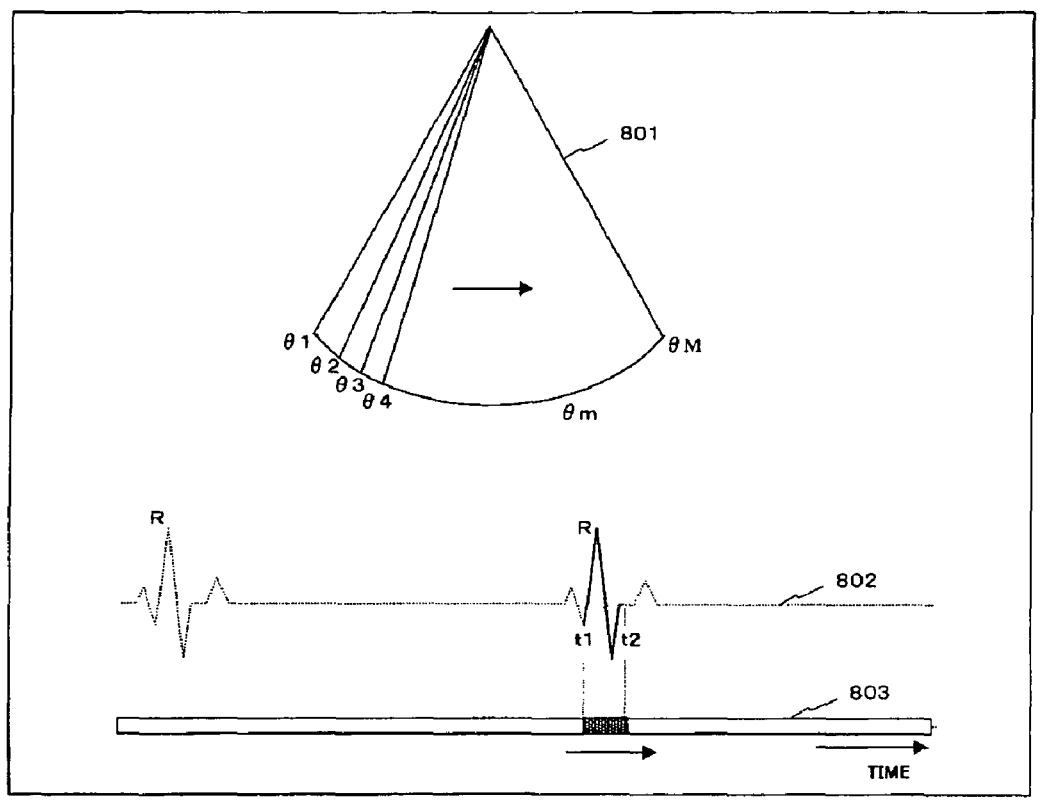
FIG. 7 is an illustration showing an example of display of B-mode image data and an ECG signal in the first embodiment.

FIG. 7 shows an exemplary illustration showing the B-mode image data and the ECG signal displayed on the display part 306. The B-mode image data 801 obtained by sector scanning is displayed with the ECG signal 802 on the same monitor. The ECG signal 802 corresponding to the timing of the B-mode image data 801, namely, the timing of t1 trough t2 when the B-mode RAW data obtained in the first scanning direction θ1 through in the Mth scanning direction θM is brightly displayed (Highlight display). A timing bar 803 indicating the t1 trough t2 of the B-mode image data 801 may be displayed under the ECG signal 802 which is continuously displayed to the timing t2.

According to the first embodiment, since the time information is added and stored in the pixel of RAW data, for example, if the header information is deleted like the image data generated after scanning conversion, the time information is not deleted. Therefore, it is possible to perform the synchronous display with the biomedical signal and the image data using the time information in the image data, for example.

Furthermore, since the common time information is added to the RAW data and the biomedical data which are stored, according to the first embodiment, the synchronous display with the image data or analysis data generated even in off-line processing of the RAW data and the biomedical signal can be performed with sufficient accuracy.

Moreover, according to the first embodiment, when the synchronization of the timing may be performed in software process, hardware can be omitted like the conventional example.

In addition, although the time information generation part 312 in the first embodiment generates the time information "1" which shows the timing of R wave of an ECG signal, or "0" otherwise, lapsed time information from the R-wave of the ECG signal may be generated as the time information.

Although the synchronous display with the ECG waveform is explained in the first embodiment as a method for indicating the timing of the B-mode image data, a marker indicating the timing of the R-wave may be displayed instead of the ECG signal waveform.

Next, a second embodiment is explained with reference to FIG. 9 and FIG. 10. In the second embodiment, a common standard time information is added to RAW data and an ECG signal, and the image data and the biomedical information are synchronously displayed based on the standard time information.

Figure 9:
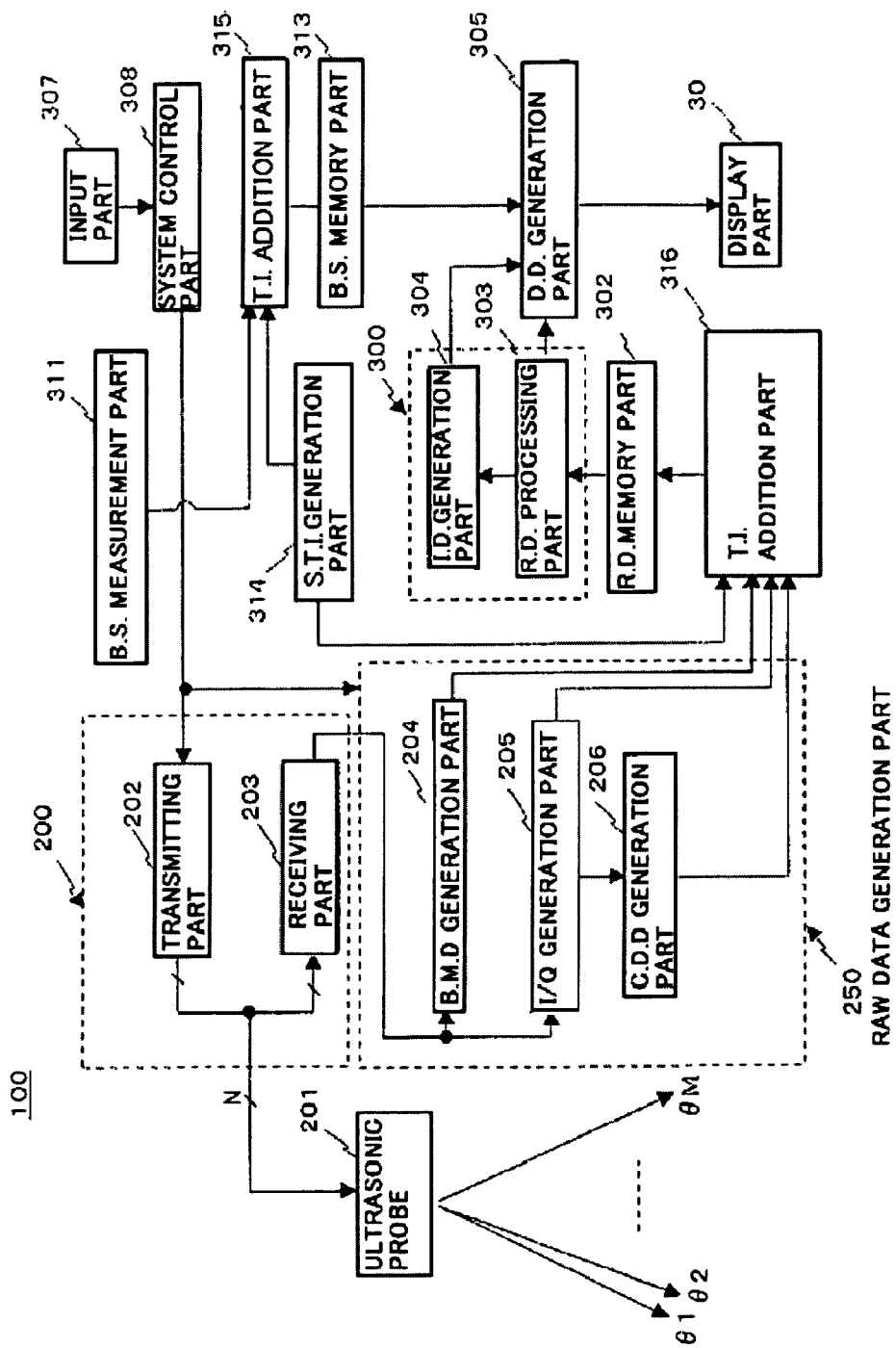
FIG. 9 is a block diagram showing a whole ultrasonic imaging apparatus in a second embodiment.

FIG. 9 is a block diagram showing a whole ultrasonic imaging apparatus 110 in the second embodiment. To simplify the explanation, the detailed explanations are omitted by attaching the same reference numbers in FIG. 9 as illustrated in FIG. 4

The ultrasonic imaging apparatus 110 of FIG. 9 includes a standard time information generating part 314 which generates standard time data, a time information addition part 316 which adds the standard time data to RAW data supplied from the RAW data generation part 250, a time information addition part 315 which adds the standard time data to the biomedical signal supplied from the biomedical signal measurement part 311 and a biomedical signal memory part 313 which stores the biomedical signal with which the standard time is added. Furthermore, the ultrasonic imaging apparatus 110 includes the same or the similar functional part as or to that of the first embodiment, such as an ultrasonic probe 201, a transceiver part 200, a RAW data generation part 250, a RAW data memory part 302, a image data/analysis data generation part 300, a display data generation part 305, a display part 306, an input part 307, and a system control part 308.

Figure 10:
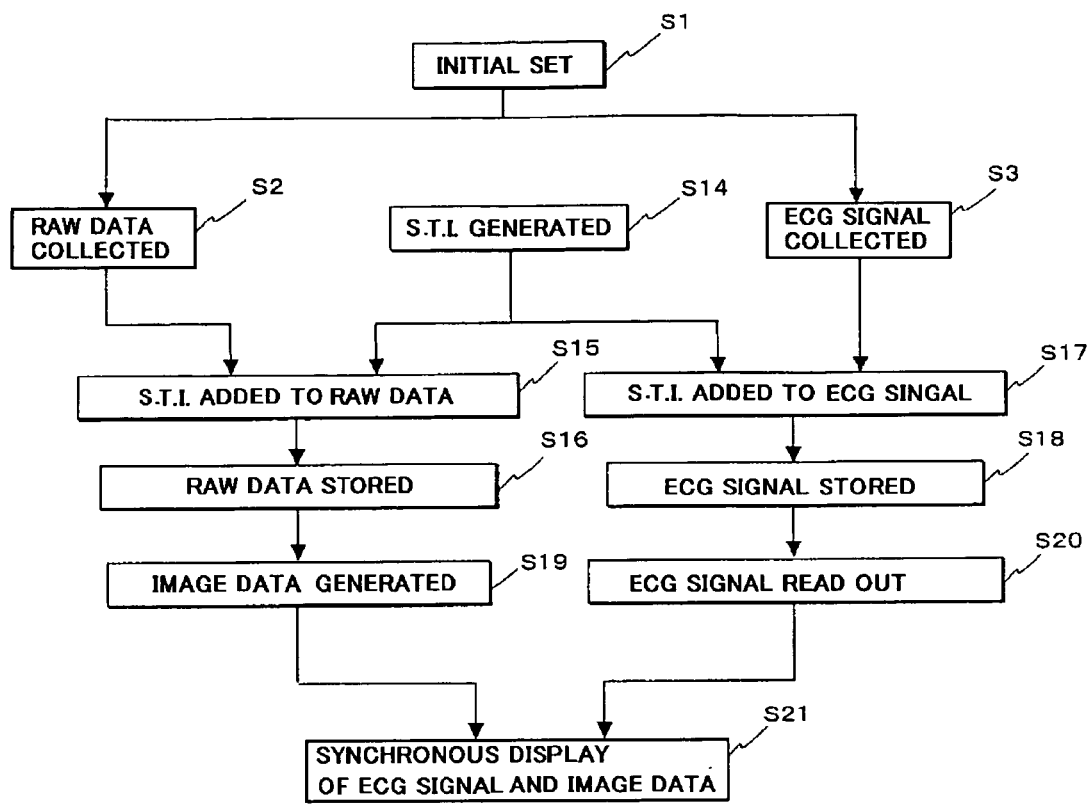
FIG. 10 is a flow chart showing a procedure of synchronized display of image data and a biomedical signal in the second embodiment.

Next, an operation of the synchronous display of the image data and the biomedical signal in the second embodiment is explained in a flow chart of FIG. 10. The synchronous display of B-mode image data and the ECG signal generated from the B-mode RAW data is explained as an example, but a synchronous display of another data may be used.

An initial set of the apparatus according to the same or the similar process of the first embodiment (Step S1 of FIG. 10), a collection of the B-mode RAW data by transmitting and receiving the ultrasonic wave in a first direction (Step S2 of FIG. 10) and a collection of the ECG signal (Step S3 of FIG. 10) are performed. The B-mode RAW data is supplied to the time information addition part 316 and the ECG signal is supplied to the time information addition part 315.

Subsequently, the time information addition part 316 adds the standard time information supplied from the standard time information generating part 314 to the time information storage area of the B-mode RAW data (Step S15 of FIG. 10). The B-mode RAW data with which the standard time information is added is stored in the RAW data memory part 302 (Step S16 of FIG. 10). Similarly, the time information addition part 315 adds the standard time information to the ECG signal, and stores the ECG signal in the biomedical signal memory part 313 (Steps S17 and S18 of FIG. 10).

Subsequently, the system control part 308 performs the ultrasonic transmission-and-reception in a second scanning direction through Mth scanning direction, further, repeats the ultrasonic transmission-and-reception in the first scanning direction through the Mth scanning direction. Each B-mode RAW data is stored in the RAW data memory part 302 with which the standard time information is added in the time information addition part 316. The ECG signal, collected in parallel to the generation and storage of the B-mode RAW data, with which the standard time information is added is stored in the biomedical signal memory part 313.

The RAW data-processing part 303 of the image data/analysis data generation part 300 reads out the B-mode RAW data in a predetermined timing based on the standard time information among the B-mode RAW data stored in the RAW data memory part 302. An image processing is performed to the read out RAW data in the RAW data-processing part 303 and subsequently, the RAW data is supplied to the image data generation part 304. The image data generation part 304 performs scanning conversion of one frame of the B-mode RAW data which is read out in the predetermined timing by the RAW data-processing part 303, and generates image data (Step S19 of FIG. 10).

The display data generation part 305 reads out the ECG signal with which the same standard time information as that of the RAW data used for generating the image data as above among the ECG signal stored in the biomedical signal memory part 313 (Step S20 of FIG. 10). The read out ECG signal is combined with the B-mode image data supplied from the image data generation part 304 of the image data/analysis data generation part 300, and display data is generated.

The display part 306 executes the D/A conversion, the television format conversion to the display data generated in the display data generation part 305, generates a display signal and displays the display signal on the monitor (Step S21 of FIG. 10).

According to the second embodiment, the common standard time information is added to the RAW data and the biomedical signal when the image data or the analysis data is generated from the RAW data obtained from the patient. Thereby, it is possible to perform the synchronous display of the image data or analysis data generated using this RAW data and the biomedical signal accurately. Moreover, according to the second embodiment, since the R-wave of the ECG signal is not used for determining the timing, for example, the processing for the synchronous display is easy.

In addition, although it is explained that the standard time is added to the header of the RAW data, the standard time information may be added to a pixel of the RAW data instead of the header as well as the first embodiment.

Next, a third embodiment is explained with reference to FIG. 11 through FIG. 14. In the third embodiment, the ECG signal collected in parallel to the generation of the RAW data by the ultrasonic transmission and reception is added to the RAW data, in order to display the image data or the analysis data and the biomedical signal are displayed synchronously.

Figure 11:
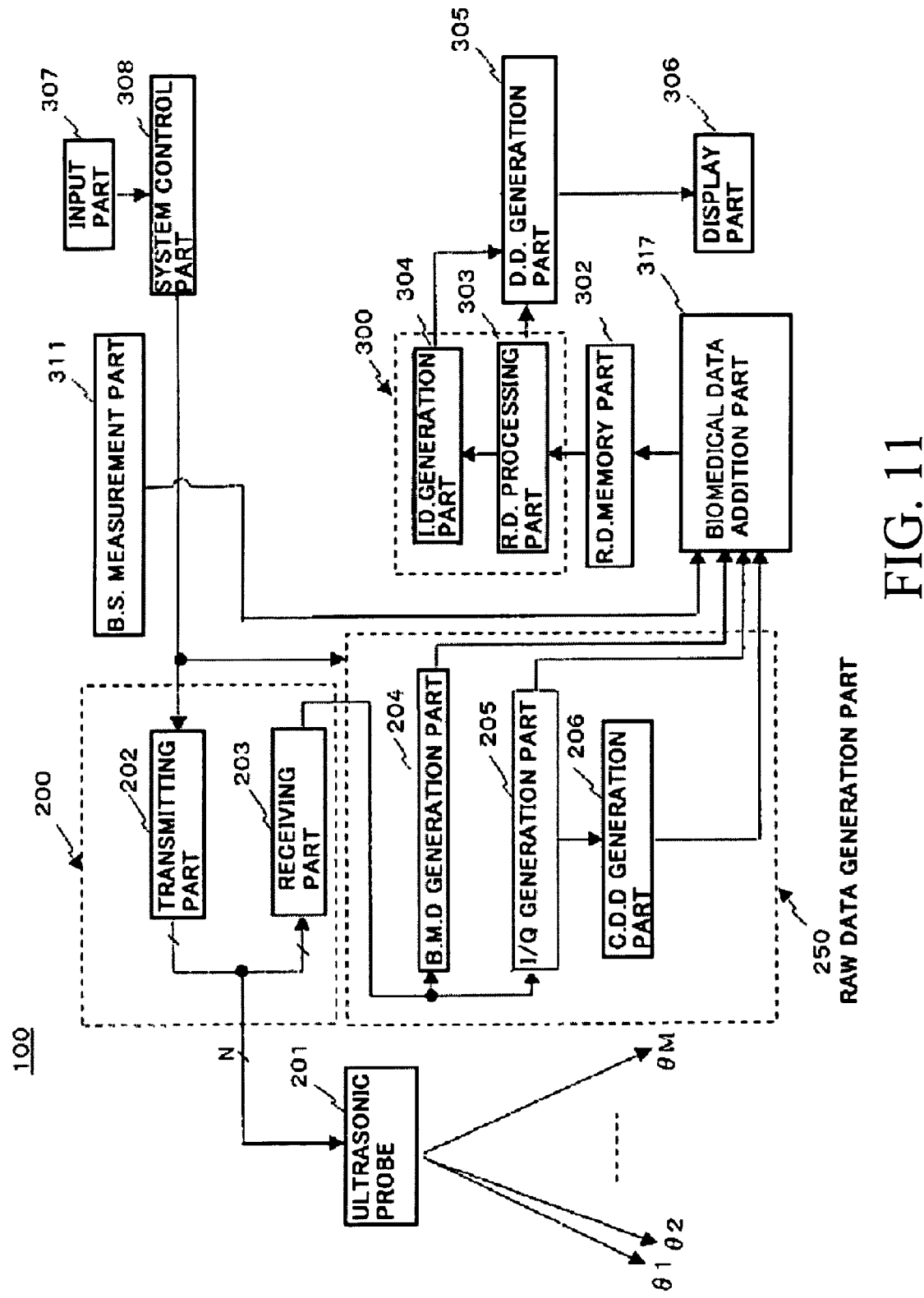
FIG. 11 is a block diagram showing a whole ultrasonic imaging apparatus in a third embodiment.

FIG. 11 is a block diagram showing a whole ultrasonic imaging apparatus 120 in the third embodiment. To simplify the explanation, the detailed explanations are omitted by attaching the same reference numbers in FIG. 11 as illustrated in FIG. 4.

The ultrasonic imaging apparatus 120 of FIG. 11 includes a biomedical data addition part 317 which adds biomedical data corresponding to the biomedical signal to the RAW data supplied from the RAW data generation part 250, and the same or similar parts of the first embodiment, such as an ultrasonic probe 201, a transceiver part 200 a RAW data generation part 250, a RAW data memory part 302, an image data/analysis data generation part 300, a display data generation part 305, a display part 306, an input part 307, and a system control part 308.

Figure 12:
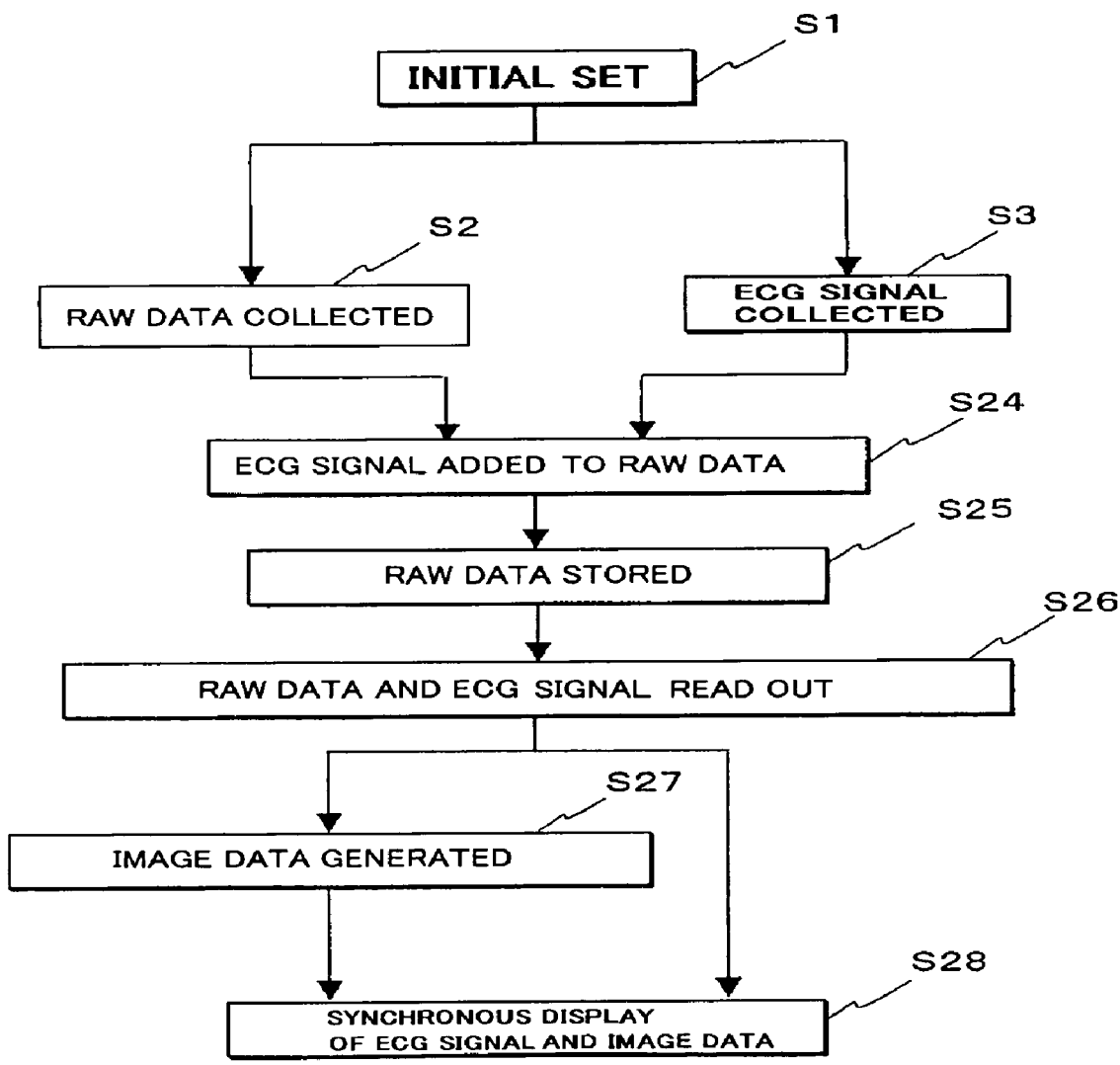
FIG. 12 is a flow chart showing a procedure of synchronized display of image data and a biomedical signal in the third embodiment.

Next, an operation of the synchronous display of the image data and the biomedical signal in the third embodiment is explained with reference to a flow chart of FIG. 12. The synchronous display of B-mode image data and the ECG signal generated from the B-mode RAW data is explained as an example, but a synchronous display of another data may be used.

An initial set of the apparatus according to the same or the similar process of the first or second embodiment (Step S1 of FIG. 12), a collection of the B-mode RAW data by transmitting and receiving the ultrasonic wave in a first direction (Step S2 of FIG. 12) and a collection of the ECG signal (Step S3 of FIG. 12) are performed. The B-mode RAW data and the ECG signal are supplied to the time biomedical data addition part 317.

The biomedical data addition part 317 changes the ECG signal supplied from the biomedical signal measurement part 311 into the ECG data. The ECG data is stored in a header or a biomedical signal storage area of pixel of the B-mode RAW data (Step S24 of FIG. 12). If the transmission and reception of the ultrasonic wave and the collection of the ECG signal are performed at substantially the same time, arrival time of the RAW data and the ECG signal to the biomedical data addition part 317 may be different due to difference of signal transfer process. In such a case, in the biomedical data addition part 317, when the ECG data is added to the RAW data, it may be necessary to take into consideration the difference in the arrival time. For example, due to a composition of system, if the ECG signal which is collected at substantially the same time as the transmission and reception of the ultrasonic wave arrives at the biomedical data addition part 317 after a predetermined period delay to the RAW data, it may be necessary to add the biomedical signal to the RAW data which arrives at the biomedical data addition part 317 the predetermined period before. For this reason, a buffer memory which stores the RAW data for more than the predetermined period temporarily is provided. The RAW data which arrives is stored in the buffer memory. If the data of one vector is written in one address in this case, the address of the buffer memory is supposed to have the following time.

$T1$=(1/pulse repetition frequency)/number of transmitting steps

Number of transmitting steps: Number of transmission necessary for generating one vector (RAW data)

If the ECG signal which is collected at substantially the same time as the RAW data arrives after T2 delay, the ECG signal which arrives at the biomedical data addition part 317 is added to the data in an address which stores past RAW data which arrives T2/T1 before the newest RAW data. When collection interval of the ECG signal is T3, the same ECG data is added to the RAW data in addresses of T3/T1. The B-mode RAW data with which the ECG data is added is stored in the RAW data memory part 302 (Step S25 of FIG. 12).

The system control part 308 performs the ultrasonic transmission-and-reception also in the second scanning direction through the Mth scanning direction, and after the Mth scanning direction, the ultrasonic transmission-and-reception is performed in the first scanning direction through Mth scanning direction repeatedly. Each B-mode RAW data, obtained at this time, with which the ECG data is added in the biomedical data addition part 317, is stored in the RAW data memory part 302.

The RAW data-processing part 303 of the image data/ analysis data generation part 300 reads out the B-mode RAW data and the ECG data in a predetermined timing among the B-mode RAW data stored in the RAW data memory part 302. The read out B-mode RAW data is supplied to the image data generation part 304, and the read out ECG data is supplied to the display data generation part 305 (Step S26 of FIG. 12). The image data generation part 304 performs the scanning conversion to one frame of the B-mode RAW data, in a predetermined timing, which is read out by the RAW data processing part 303, and generates one frame of the B-mode image data to be supplied to the display data generation part 305 (Step S27 of FIG. 12).

The display data generation part 305 combines the ECG data supplied from the RAW data processing part 303 and the B-mode image data supplied from the image data generation part 304 to generate display data. The display part 306 executes the D/A conversion, the television format conversion to the display data generated in the display data generation part 305, generates a display signal and displays the display signal on the monitor (Step S28 of FIG. 12).

Figure 13:
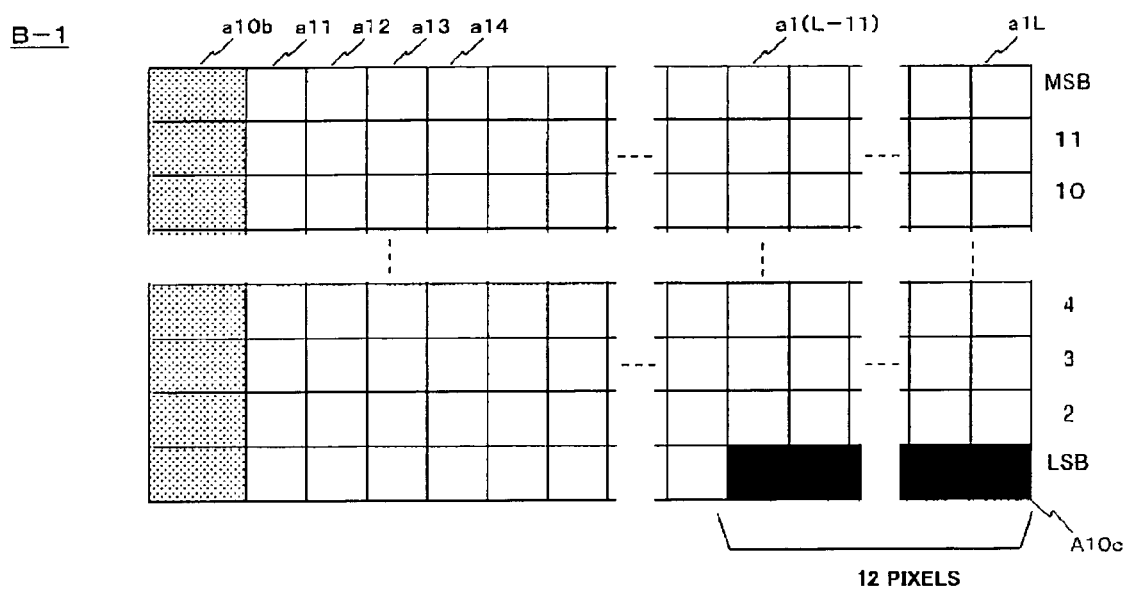
FIG. 13 is an illustration showing a composition of RAW data with a biomedical signal is added in the third embodiment.

FIG. 13 is an illustration showing a composition of the B-mode RAW data in the third embodiment For example, each pixel of a11 to a1L of B-mode RAW data B-1 which is obtained in a first direction θ1 is 12 bits, and LSB pixels of 12 bits of a1 (L-11) through a1 of the B-mode RAW data B-1 is set as biomedical data storage area a10c. That is, the ECG data of 12 bits supplied from the biomedical signal measurement part 311 of FIG. 11 is stored at the biomedical data storage area a10c. In addition, since the biomedical signal storage area a10c mainly includes LSB of each pixel like FIG. 8, the influence to quality of image of the B-mode image data is small.

Figure 14:
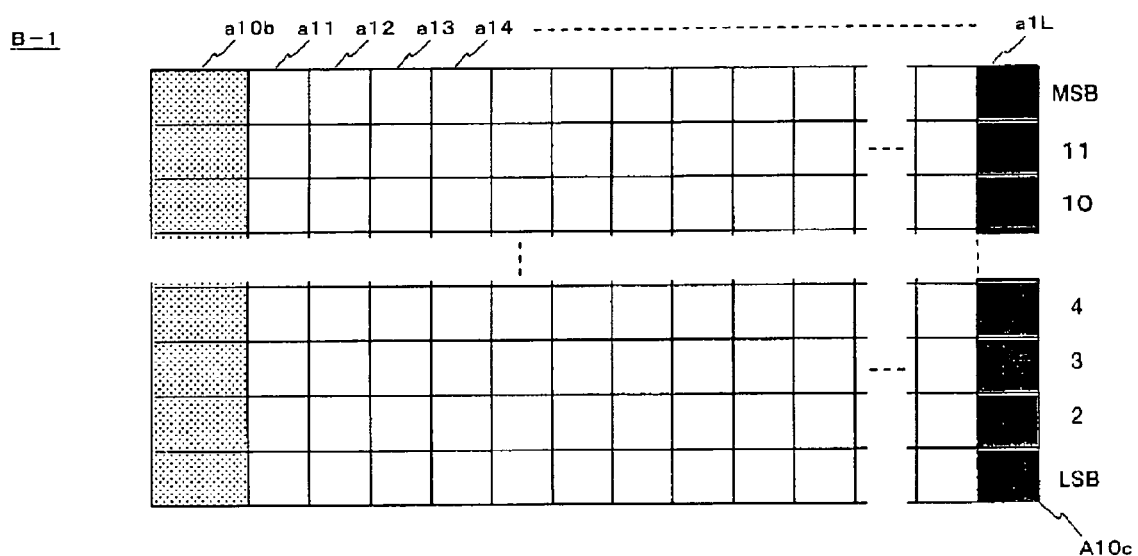
FIG. 14 is an illustration showing a composition of RAW data with a biomedical signal is added in the third embodiment.

FIG. 14 shows a modification of composition of the RAW data, and each pixel a11 through a1L of the B-mode RAW data obtained in the first scanning direction θ1 is 12 bits like FIG. 13. Pixels a1L of 12 bits of LSB through MSB of the B-mode RAW data B-1 are set as the biomedical signal storage area a10c. In this case, since the ECG data is stored in all of pixel a1L, it is desired that a blanking processing is performed not to display the pixel a1L when the B-mode image data is displayed. Moreover, the number of pixels of the B-mode RAW data B-1 may be increased from L pieces, and a1 (L+1) may be set as the biomedical signal storage. Moreover, the data may be stored in a header or footer in which other addition information exists.

According to the third embodiment, the ECG signal obtained in parallel to the collection of the RAW data is added to the RAW data as the ECG data when the image data or the analysis data is generated. Thereby, the synchronous display of the image data or the analysis data and the biomedical signal is easily and precisely performed Furthermore, in the third embodiment, since it is not necessary to add the time information to the ECG signal, the apparatus can be simplified.

Although embodiments and modifications are explained above, the present invention may be not limited to the above embodiments and modifications, and other various modifications may be made. For example, it is explained in the above embodiment that the B-mode image data obtained from the B-mode RAW data is synchronously displayed with the ECG signal, however other biomedical signal may be displayed with other image data or analysis data, such as the Color Doppler image data and the Doppler Spectrum data. Moreover, the above-mentioned biomedical signal may be a brain wave, a heartbeat, a blood-pressure waveform, a respiratory waveform, an impedance waveform, etc.

Especially, it is suitable to adopt a distributed value pixel with comparatively low operating frequency and importance when the time information or the biomedical signal is added to pixel of the Color Doppler RAW data.

Moreover, although it is explained in the above embodiments that the RAW data is a unit of data in the scanning direction (namely, vector data), the RAW data may not be limited to such data and the RAW data may be ultrasonic data before scan conversion. Although it is explained in the above embodiments that the biomedical signal measurement part used for generating the time information is a part of the ultrasonic imaging apparatus, an independent biomedical signal measurement part may be adapted.

Furthermore, although it is explained in the above embodiments that single image data or single analysis data is displayed with a single biomedical signal, a plurality of image data or analysis data may be displayed with a plurality of biomedical signals.

In addition, although it is explained in the above embodiments that the transceiver part is an analog type, a digital type may be used. Moreover, although it is explained in the above embodiments that the RAW data is two dimension, three dimensional data may be used. In order to collect the 3-dimensional RAW data, it is suitable that the ultrasonic probe has ultrasonic transducers which are 2-dimensionally arranged.

What is claimed is:

1. An ultrasonic imaging apparatus, comprising:
an ultrasonic probe including a plurality of ultrasonic transducers which perform ultrasonic transmission and reception to an object;
a transceiver unit configured to obtain an ultrasonic signal from the object by driving the plurality of ultrasonic transducers;
an ultrasonic data generation unit configured to generate raw pixel data based on the ultrasonic signal;
a time information generation unit configured to generate time information related to the ultrasonic transmission or reception; and
a time information addition unit configured to add the time information to only a least significant bit of the raw pixel data.

2. The ultrasonic imaging apparatus according to claim 1, further comprising a biomedical signal measurement unit configured to measure a biomedical signal of the object.

3. The ultrasonic imaging apparatus according to claim 2, further comprising an image/analysis data generation unit configured to generate at least one of image data and analysis data based on the ultrasonic data and the time information.

4. The ultrasonic imaging apparatus according to claim 3, further comprising a display unit configured to synchronously display biomedical data corresponding to the biomedical signal and at least one of the image data and the analysis data based on the time information.

5. The ultrasonic imaging apparatus according to claim 4, wherein the time information generation unit generates the time information based on the biomedical signal.

6. The ultrasonic imaging apparatus according to claim 5, wherein the time information generation unit generates the time information based on a timing of an organ, the timing detected based on the biomedical signal.

7. The ultrasonic imaging apparatus according to claim 5, wherein the time information generation unit generates the time information based on R-wave of an ECG signal collected from the object.

8. The ultrasonic imaging apparatus according to claim 4, wherein the ultrasonic data generation unit generates B-mode data based on the ultrasonic signal.

9. The ultrasonic imaging apparatus according to claim 4, wherein the ultrasonic data generation unit generates Color Doppler data based on the ultrasonic signal.

10. The ultrasonic imaging apparatus according to claim 4, wherein the ultrasonic data generation unit generates Doppler Spectrum data based on the ultrasonic signal.

11. The ultrasonic imaging apparatus according to claim 1, wherein the time information addition unit is configured to add the time information to only the least significant bit of the raw pixel data, wherein the raw pixel data has smaller volume of data than one frame.

12. The ultrasonic imaging apparatus according to claim 1, wherein the time information addition unit adds the time information to each raster data.

13. An ultrasonic imaging apparatus, comprising:
an ultrasonic probe including a plurality of ultrasonic transducers which perform ultrasonic transmission and reception to an object;
a transceiver unit configured to obtain an ultrasonic signal from the object by driving the plurality of ultrasonic transducers;
an ultrasonic data generation unit configured to generate ultrasonic raw pixel data based on the ultrasonic signal;
a standard time information generation unit configured to generate standard time information;
a biomedical signal measurement configured to measure a biomedical signal of the object;
a first time information addition unit configured to add the standard time information to only a least significant bit of the raw pixel data; and
a second time information addition unit configured to add the standard time information to biomedical data corresponding to the biomedical signal.

14. The ultrasonic imaging apparatus according to claim 13, further comprising an image/analysis data generation unit configured to generate at least one of raw pixel image data and analysis data based on the standard time information.

15. The ultrasonic imaging apparatus according to claim 14, further comprising a display unit configured to synchronously display the biomedical data corresponding to the biomedical signal and at least one of the image data and the analysis data based on the standard time information.

16. The ultrasonic imaging apparatus according to claim 15, wherein the biomedical signal measurement measures an ECG signal of the object.

17. The ultrasonic imaging apparatus according to claim 15, wherein the ultrasonic data generation unit generates B-mode data based on the ultrasonic signal.

18. The ultrasonic imaging apparatus according to claim 15, wherein the ultrasonic data generation unit generates Color Doppler data based on the ultrasonic signal.

19. The ultrasonic imaging apparatus according to claim 15, wherein the ultrasonic data generation unit generates Doppler Spectrum data based on the ultrasonic signal.

20. The ultrasonic imaging apparatus according to claim 13, wherein the standard time information addition unit adds the standard time information to each raw pixel data which has smaller volume of data than one frame.

21. The ultrasonic imaging apparatus according to claim 13, wherein the standard time information addition unit adds the standard time information to each raster data.

22. The ultrasonic imaging apparatus according to claim 13, wherein the standard time information addition unit adds the standard time information in a header of the raw pixel data.

23. An ultrasonic imaging apparatus, comprising:
an ultrasonic probe including a plurality of ultrasonic transducers which perform ultrasonic transmission and reception to an object;
a transceiver unit configured to obtain an ultrasonic signal from the object by driving the plurality of ultrasonic transducers;
an ultrasonic data generation unit configured to generate raw pixel data for a plurality of pixels, based on the ultrasonic signal;
a biomedical signal measurement configured to measure a biomedical signal of the object; and
a biomedical data addition unit configured to add biomedical data corresponding to the biomedical signal to the raw pixel data by adding the biomedical signal to only a least significant bit of the raw pixel data of at least one of the plurality of pixels with the biomedical data.

24. The ultrasonic imaging apparatus according to claim 23, further comprising an image/analysis data generation unit configured to generate at least one of image data and analysis data based on the raw pixel data.

25. The ultrasonic imaging apparatus according to claim 24, further comprising a display unit configured to synchronously display the biomedical data corresponding to the biomedical signal and at least one of the image data and the analysis data.

26. The ultrasonic imaging apparatus according to claim 25, wherein the biomedical signal measurement measures an ECG signal of the object.

27. The ultrasonic imaging apparatus according to claim 25, wherein the ultrasonic data generation unit generates B-mode data based on the ultrasonic signal.

28. The ultrasonic imaging apparatus according to claim 25, wherein the ultrasonic data generation unit generates Color Doppler data based on the ultrasonic signal.

29. The ultrasonic imaging apparatus according to claim 25, wherein the ultrasonic data generation unit generates Doppler Spectrum data based on the ultrasonic signal.

30. A method for ultrasonic imaging, comprising:
performing ultrasonic transmission and reception to an object by an ultrasonic probe including a plurality of ultrasonic transducers;
obtaining an ultrasonic signal from the object by driving the plurality of ultrasonic transducers;
generating ultrasonic raw pixel data based on the ultrasonic signal;
generating standard time information;
measuring a biomedical signal of the object;
adding the standard time information only to a least significant bit of the raw data; and
adding the standard time information to biomedical data corresponding to the biomedical signal.

31. An ultrasonic imaging apparatus, comprising:
an ultrasonic probe including a plurality of ultrasonic transducers which perform ultrasonic transmission and reception to an object;
a transceiver unit configured to obtain an ultrasonic signal from the object by driving the plurality of ultrasonic transducers;
an ultrasonic data generation unit configured to generate raw pixel data for a plurality of pixels, based on the ultrasonic signal;
a biomedical signal measurement configured to measure a biomedical signal of the object; and
a biomedical data addition unit configured to add biomedical data corresponding to the biomedical signal to the raw pixel data by adding the biomedical signal to only a least significant bit of the raw pixel data of at least one of the plurality of pixels with the biomedical data, under a condition where an addition timing of the biomedical signal to the ultrasonic data is adjusted based on a condition of the ultrasonic transmission and reception.

32. The ultrasonic imaging apparatus according to claim 31, wherein the biomedical data addition unit includes a memory configured to temporally store the raw pixel data.

* * * * *